United States Patent [19]

Fawcett

[11] Patent Number: 6,165,736
[45] Date of Patent: *Dec. 26, 2000

[54] METHOD OF DETECTING BACTERIAL INFECTION

[75] Inventor: Paul Thomas Fawcett, Rising Sun, Md.

[73] Assignee: The Nemours Foundation, Wilmington, Del.

[*] Notice: This patent issued on a continued prosecution application filed under 37 CFR 1.53(d), and is subject to the twenty year patent term provisions of 35 U.S.C. 154(a)(2).

[21] Appl. No.: 09/123,231

[22] Filed: Jul. 28, 1998

[51] Int. Cl.$^7$ .......................... A61K 39/02; G01N 33/53; C07H 21/04; C07K 14/195; C12N 1/21

[52] U.S. Cl. ................. 435/7.32; 424/184.1; 424/234.1; 435/4; 435/7.1; 435/69.1; 435/71.2; 435/252.3; 435/320.1; 536/23.7

[58] Field of Search .............................. 424/184.1, 234.1; 435/4, 7.1, 7.32, 69.1, 71.2, 252.3, 320.1; 536/23.7

[56] References Cited

U.S. PATENT DOCUMENTS

| | | | |
|---|---|---|---|
| 5,262,156 | 11/1993 | Alemohammad | 424/92 |
| 5,314,804 | 5/1994 | Boguslaski et al. | 435/12 |
| 5,420,014 | 5/1995 | Cripps et al. | 435/7.32 |
| 5,420,016 | 5/1995 | Boguslaski et al. | 435/12 |
| 5,434,253 | 7/1995 | Thompson et al. | 536/23.2 |
| 5,439,801 | 8/1995 | Jackson | 435/12 |
| 5,477,854 | 12/1995 | Essen-Moller | 128/635 |
| 5,498,528 | 3/1996 | King | 435/34 |
| 5,542,419 | 8/1996 | Moulton-Barrett et al. | 128/650 |
| 5,770,719 | 6/1998 | Kapoor et al. | 536/24.1 |

OTHER PUBLICATIONS

SuperCos 1 Cosmid Vector Kit Instruction Manual, Catalog #251301 Revision #047001d, Stratagene Cloning Systems, LaJolla, CA.

Fawcett, P.T., Correlation of Seroreactivity with Response to Antibiotics in Pediatric Lyme Borreliosis, Clinical and Diagnostic Laboratory Immunology, vol. 4, No. 1, Jan. 1997, pp. 85–88.

Fawcett, P.T., et al., Frequency and Specificity of Antibodies that Crossreact with *Borrelia burgdorferi* Antigens, The Journal of Rheumatology, 19:4, 1992, pp. 592–587.

Fawcett, P.T., et al., Detection of Antibodies to the Recombinant P39 Protein of *Borrelia burgdorferi* Using Enzyme Immunoassay and Immunoblotting, The Journal of Rheumatology, 20:4, 1993, pp. 734–738.

Fawcett, P.T., et al., Comparative Evaluation of Adsorption with E. Coil on ELISA Test for Lyme Borreliosis, The Journal of Rheumatology, 22:4, 1995, pp. 684–688.

*Primary Examiner*—Phuong T. Bui
*Attorney, Agent, or Firm*—McGuireWoods, LLP

[57] ABSTRACT

A method of developing sensitive and discriminatory diagnostic procedures for detecting active bacterial infection in animals, especially humans, basically involves partially digesting the genomic DNA of the infecting bacterial pathogen into a generally large number of ideally random fragments and finding proteins encoded by those fragments which evoke a discriminating response to specimens from viably infected animals. Cloning techniques are used to cause the genes of the multitude of DNA fragments to produce proteins. Groups of proteins encoded by the genes of each fragment are separately tested for the ability to generate an immune response in certain specimens from animals known to have "viable infection", "convalescent infection" and "naive status" with respect to infection by the infecting bacterial pathogen. The protein groups which evoke positive immune responses to viably infected but no immune response to naive specimens are identified as "selectively responsive proteins". Similarly, selectively responsive proteins which are found to evoke no immune response from convalescent specimens are identified as "discriminatingly responsive proteins". These selectively and discriminatingly responsive protein groups can be cloned in magnitude and used to test unknown patients for status of infection.

The method is amenable for developing tests based upon non-invasively obtained specimens, such as peripherally-obtained blood samples. Moreover, rigorous mapping of the pathogen genome is not prerequisite for carrying out the development method. Consequently, the development method can be used to obtain diagnostic procedures particularly suitable for generating individually inexpensive bacterial infection assays capable for screening large scale patient populations.

18 Claims, 1 Drawing Sheet

METHOD OF DETECTING BACTERIAL INFECTION

FIELD OF THE INVENTION

This invention relates to a method of developing a diagnostic procedure for determining whether a patient has a viable bacterial infection. More specifically, it relates to a serologic test for determining if the patient is viably infected with *Helicobacter pylori*.

BACKGROUND AND SUMMARY OF THE INVENTION

The ability to diagnose bacterial infection is an important aspect of modem medicine. Frequently, a patient's symptoms alone are insufficient to indicate either that an infection is the cause of an illness or to identify the specific pathogen when bacterial infection is suspected. Diagnostic methods are constantly being devised to more accurately evaluate bacterial infections.

Many techniques for developing methods for diagnosing bacterial infection involve the approach of analyzing a specimen taken from a patient for a telltale characteristic. For example, the specimen can be analyzed for the pathogen directly, or for a biochemical product that indirectly indicates the presence of the pathogen in the patient's body. Biopsy or similarly difficult or painful sampling procedure is sometimes required to obtain the required specimen. This is often necessary for digestive system infections which target organs located deep within the body.

Recent developments in the field of biotechnology permit diagnosis for infection by analyzing non-invasively obtained specimens, such as blood serum, urine, mucous discharges and the like. A favored traditional approach to developing such diagnostic methods typically entails several steps that include (i) biochemically mapping the infecting organism in detail; (ii) isolating and/or synthesizing specific biochemical fragments identified by the mapping or antigens produced by the organism; (iii) exposing a specimen from the patient to the specific biochemical fragments or antigens; (iv) testing for a reaction to the exposure; and (v) confirming that the specific biochemical fragments or antigens are exclusive to the infecting organism. Step (i) usually requires an exhaustive and thorough analysis of the bacteria and how it affects the patient. Step (v) is necessary to rule out false positive diagnoses based upon response to extraneously introduced fragments. Generally these steps (i) and (v) are complicated, require a high level of biomedical skill, and can take a very long time to accomplish.

The traditional technique of developing bacterial infection diagnostic procedures is further hindered by the inherent nature of antibodies to remain permanently in the body. Diagnostic procedures developed in the customary way often determine interaction between specific antibodies and antigens previously found to be associated with the infecting organism. Because antibodies can remain detectable in the host indefinitely, a convalescent patient who was previously successfully treated for the infection but is not presently viably infected is likely to generate an interactive response when tested by such a conventionally developed diagnostic procedure. The procedure cannot distinguish between the existence of a viable infection and a not presently symptomatic (i.e., "inactive") infection. Thus, the traditional approach suffers from the drawback that it ultimately might not lead to a successful result.

A simple and efficient method for developing highly discriminatory and sensitive diagnostic procedures for bacterial infection is very desirable. Such a method which includes the ability to easily develop diagnostic procedures that can distinguish active infections from inactive infections as well as from non-infections has been discovered. The new method has been demonstrated by example in the context of developing a procedure for diagnosing active infections of *Helicobacter pylori*.

*Helicobacter pylori* (hereinafter, "Hp") is a rod-shaped bacterium which infects the gastric mucosa. Infection by Hp is a leading cause of certain gastric diseases such as duodenal ulcers and gastric ulcers. The bacterium also has been implicated in development of gastric cancer. Symptoms of Hp infection vary from mild to severe and can include abdominal pain, nausea, indigestion, gas and bloating. Some of these symptoms are similar to those of unrelated health conditions such as simple indigestion and chronic dyspepsia. Thus a method for detecting Hp should be both sensitive and discriminatory to accurately identify the nature of a patient's illness.

Various methods of diagnosing Hp infection have been developed. For example, Hp can be detected by culture assay or by the Campylobacter-like organism ("CLO") test described in U.S. Pat. No. 4,748,113, incorporated herein by reference. Both test types require obtaining a sample by highly invasive, endoscopic biopsy. Culturing methods additionally are time consuming and produce variably successful diagnoses. Faster CLO analysis detects urease produced by Hp. However, the enzyme can be present due to causes other than Hp. Thus CLO testing usually is not adequately specific for detecting the presence of the Hp pathogen. Certain non-invasive Hp diagnostic methods have also been developed. These include breath tests that determine the presence of ureas associated with Hp infection. Such methods detect radioactive and non-radioactive carbon isotope-bearing urea compounds. Difficulty introduced by the need to control hazardous materials is an obvious shortcoming of the radioactive carbon test. Breath tests generally are reported to be adequately sensitive and reliably specific for Hp. Unfortunately, conduct of the such tests is labor intensive and requires many minutes of patient participation. These characteristics render breath tests impractical for screening the very large potential patient populations which are susceptible to Hp infection. Also, specialized equipment not usually installed in most present-day clinical laboratories is necessary to carry out breath tests.

Enzyme-linked immunosorbent assay ("ELISA") is a serologic test applicable to Hp detection. ELISA analysis would seem well suited to Hp diagnosis because it is fast, non-labor intensive, uses samples obtained quickly without discomfort or inconvenience of the patient, and employs inexpensive equipment and materials. Unfortunately, ELISA-based tests are not as sensitive as other diagnostic methods. Furthermore, ELISA tests analyze for antibodies produced by Hp infection rather than the presence of the bacteria directly. The antibodies can remain present in the patient long after Hp has been eliminated, for example by prior antibiotic treatment. Consequently, ELISA analysis cannot reliably distinguish between a viable Hp infection and a previously treated, presently non-symptomatic, inactive infection.

There is great need for a very sensitive and highly specific diagnostic procedures capable of detecting bacterial infections generally, and Hp infection in particular. The present invention now provides a method that can be applied to diverse pathogen-patient systems to develop new diagnostic procedures for detecting bacterial infections. The new diagnostic procedure development method can be applied in situations involving an infecting bacterial pathogen which engenders an immune response in an infected patient animal. Accordingly, there is provided a method of developing a diagnostic procedure for detecting infection of an animal by an infecting bacterial pathogen comprising the steps of:

(A) verifying that the infecting pathogen is capable of generating an immune response to a specimen bearing antibodies from an animal known to have a viable infection of the infecting bacterial pathogen;

(B) Providing a plurality of groups of at least one protein encoded by a gene of a random fragment of the genomic DNA of the infecting bacterial pathogen;

(C) obtaining a known specimen bearing antibodies from an animal known to have a viable infection of the infecting bacterial pathogen;

(D) separately contacting the groups of proteins with a portion of the known specimen;

(E) identifying as a positively responsive group, each group of proteins which evokes a positive immune response to contact with the known specimen;

(F) obtaining a first control specimen bearing antibodies from an animal known to be naive with respect to infection by the infecting bacterial pathogen;

(G) separately contacting positively responsive groups of proteins with a portion of the first control specimen; and (H) identifying as a selectively responsive group, each of the positively responsive groups of proteins which evokes no immune response to contact with the first control specimen.

In a particular aspect of this invention, a method for verifying the immune response has been identified. The verifying steps include:

breaking up the whole pathogen into random portions;

obtaining a classed sample from a patient known have a viable infection of the infecting bacterial pathogen;

testing by immunoassay each of the random portions for an immune response to the classed sample; and observing a positive immunoassay result for at least some of the portions.

The present invention further provides a novel diagnostic procedure for detecting bacterial infection in a patient animal developed by the above method. The new diagnostic procedure features the ability to use minimally invasively obtained specimens from a patient to differentiate between a viable, convalescent infection and naive states with respect to infection by a pathogen of interest. Hence, the diagnostician can determine whether those cases in which the pathogen has been eliminated from the patient although long-lived antibodies remain resident. Additionally, the novel diagnostic procedure developed according to the present invention advantageously is easy to implement, uses commonly available laboratory materials, provides a fast result and therefore is amenable to screening large numbers of potential patients rapidly and inexpensively. Still further according to this invention there is provided a method of diagnosing a viable infection of an animal by an infecting bacterial pathogen comprising contacting blood serum from the animal with a selectively responsive protein and/or a discriminatingly responsive protein.

There is especially provided such a diagnostic method for the detection of *Helicobacter pylon* infection.

Through application of the novel diagnostic method development procedure there can be obtained a composition suitable for use in diagnosing active bacterial infections. Thus there are also provided compositions for use in a diagnostic procedure for detecting an infection of an animal by an infecting bacterial pathogen that engenders an immune response wherein a composition comprises a selectively responsive protein and another composition comprises a discriminatingly responsive protein. The selectively responsive protein and discriminatingly responsive protein are proteins encoded by fragments of the genomic DNA of the infecting bacterial pathogen. These compositions can be obtained by a method comprising the steps of:

(A) verifying that the infecting pathogen is capable of generating an immune response to a specimen bearing antibodies from an animal known to have a viable infection of the infecting bacterial pathogen;

(B) Providing a plurality of groups of at least one protein encoded by a gene of a random fragment of the genomic DNA of the infecting bacterial pathogen;

(C) obtaining a known specimen bearing antibodies from an animal known to have a viable infection of the infecting bacterial pathogen;

(D) separately contacting the groups of proteins with a portion of the known specimen;

(E) identifying as a positively responsive group, each group of proteins which evokes a positive immune response to contact with the known specimen;

(F) obtaining a first control specimen bearing antibodies from an animal known to be naive with respect to infection by the infecting bacterial pathogen;

(G) separately contacting positively responsive groups of proteins with a portion of the first control specimen;

(H) identifying as a selectively responsive group, each of the positively responsive groups of proteins which evokes no immune response to contact with the first control specimen;

(I) obtaining a second control specimen bearing antibodies from an animal known to be convalescent with respect to infection by the infecting bacterial pathogen;

(J) separately contacting selectively responsive groups of proteins with a portion of the second control specimen; and (K) identifying as a discriminatingly responsive group, each of the selectively responsive groups of proteins which evokes no immune response to contact with the second control specimen.

Appreciating that a key ingredient of the composition useful for detecting bacterial infections is a protein encoded by the genomic DNA of the infecting pathogen, there has been discovered a way to produce colonies of mutant organisms with the ability to produce selectively responsive and discriminatingly responsive proteins. Thus there is also provided a method of producing cloned host bacteria capable of producing protein useful for diagnosing a patient animal for infection by an infecting bacterial pathogen that engenders an immune response. And yet further, there is provided a cloned host bacteria for making a reagent of a diagnostic procedure for detecting such infections. The cloned host bacteria of a species other than the infecting bacterial pathogen comprises a transfected fragment of genomic DNA of the infecting bacterial pathogen that encodes a selectively responsive protein or a discriminatingly responsive protein.

DETAILED DESCRIPTION

Figure 1:
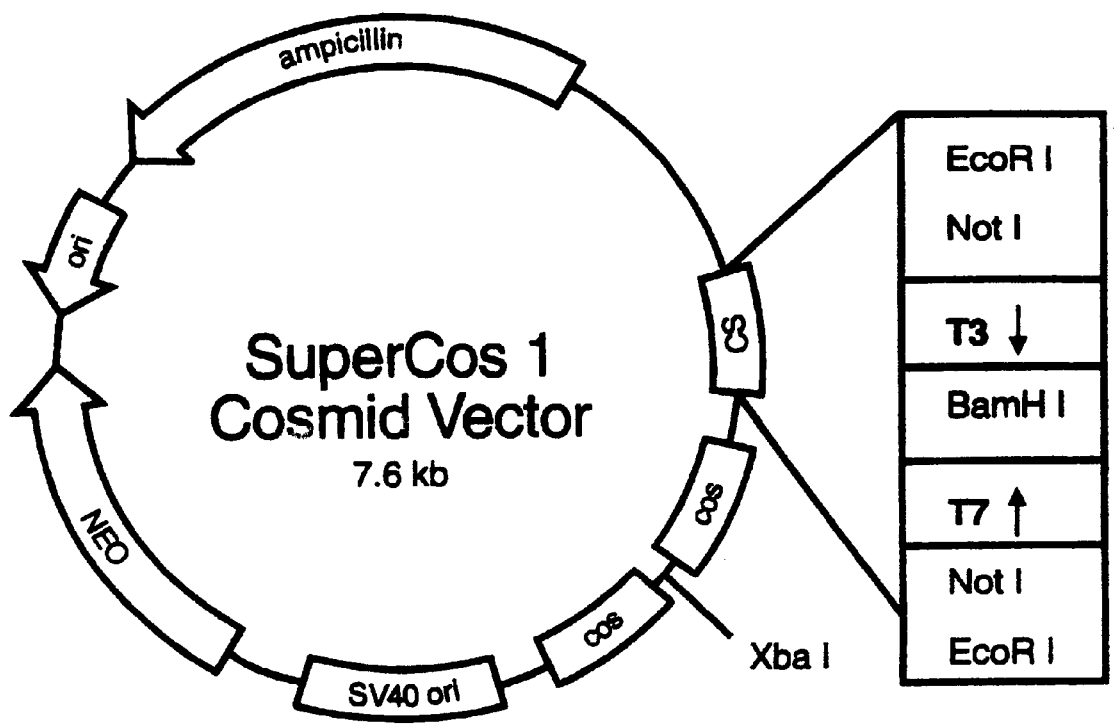
FIG. 1 is a diagram of the gene map of SuperCos I cosmid.

In one aspect, the present invention provides a novel method that can be used to develop a procedure for diagnosing the state of infection by an infecting bacterial pathogen. The method will yield an effective diagnostic procedure for any particular infecting bacterial pathogen which engenders an immune response. The term "engenders an immune response" means that infection by the pathogen results in the production in the infected organism of cells capable of directly interacting with the infecting bacterial pathogen or a component of it, or of cells which produce proteins (e.g., immunoglobulins) that are directly capable of reacting with the infecting bacterial pathogen or a component of it. As can well be appreciated by one of ordinary skill in the art, the exact number and identification of all such bacterial strains is not presently known.

Thus it is well advised as preliminary to applying the novel method to perform a screening analysis to assure that the bacterial pathogen responsible for the infection of interest indeed can produce an immune response.

The screening can be accomplished by breaking up the whole pathogen into its component proteins. The protein components are then tested for immune response with classed samples, such as classed sera specimens from patients known to be "viably infected" with the infecting pathogen. Any of the well known immunoassay protocols can be used, such as Western Blot, ELISA, "immunodot", latex agglutination and nephelometry. If at least some of the component proteins produce a positive reaction to the classed samples, it may be concluded that an immune response of diagnostic significance exists. Representative bacterial infections for which the novel method can be used to develop diagnostic procedures include *Helicobacter pylon,* and *Borrelia burgdorferi.*

The diagnostic procedure developed by the novel method can distinguish between the viable, convalescent and naive states with respect to infection by the particular bacterial pathogen of interest. Thus the tendency of the procedure to generate false positive diagnoses should be minimized. The term "viable infection" means a current infection wherein the infecting bacterial organisms are present and alive in the patient at the time of diagnosis. The term "convalescent infection" refers to the present state of a non-symptomatic patient (occasionally referred to as a "convalescent patient") who has in the past experienced a viable infection by the same infecting bacterial pathogen who either has been successfully treated or has naturally overcome the prior bacterial infection. As a result, the patient's immune system usually possesses residual antibodies to the infecting bacterial pathogen. According to the novel method, these antibodies can be distinguished from antibodies in or from individuals with viable infection. Lastly, the term "naive" with respect to state of infection refers to the status of a patient who has neither viable or convalescent state infection. That is, the naive status patient's immune system does not contain either living bacteria or antibodies for the particular infecting bacterial pathogen.

Once there is assurance that the bacterial pathogen does engender an immune response, the novel method involves producing an expression library of a generally large number of genes selected at random from the infecting bacterial pathogen genome. Preferably, the expression library is made by partially digesting the genomic DNA of the infecting bacterial pathogen into many ideally random fragments. The expression library samples are manipulated, for example by cloning techniques, to provide corresponding samples of protein(s) encoded by the gene(s) on the fragments. Due to the random fragmentation, each fragment may have one, more than one or no genes capable of producing proteins. With respect to these proteins, the term "group" is used herein to refer to the one or more of such proteins which may be produced by any particular fragment.

The groups of proteins produced from the fragments are separately tested to determine whether they can be recognized by an immune response to a specimen from an infected animal. Preferably in successive order, positively responsive protein groups, selectively responsive protein groups and discriminatingly responsive protein groups are identified from among all the groups. The term "positively responsive protein group" means a group of proteins which evokes a positive response to contact with a specimen from an animal having a viable infection of the infecting bacterial pathogen. The term "selectively responsive protein group" means a positively responsive protein group which evokes no response to contact with a specimen from an animal that is not then or previously infected. That is, a selectively responsive protein group will induce a positive response to a viable infection and also will fail to induce a positive response to a naive state specimen. The term "discriminatingly responsive protein group" means a selectively responsive protein group which evokes no response to a specimen from a convalescent animal. Thus a selectively responsive protein group can be used to test a patient to distinguish viable and/or convalescent state infection from naive state infection. Furthermore, a discriminatingly responsive protein group can distinguish between a viable and a convalescent state infection. A two stage protocol that employs both selectively and discriminatingly responsive protein groups will be able to accurately diagnose the state of infection.

Traditional diagnostic method development usually focuses upon mapping the DNA of the infecting bacterial pathogen to identify specific proteins produced by the infecting organism. After verifying that these are unique markers for the health condition targeted for detection, an assay is developed that is highly sensitive and specific for detecting the identical markers in a specimen of a patient. In contrast, this invention is based upon breaking up the genomic DNA of the infecting organism randomly in that many fragments containing different protein-encoding genes are obtained in separate expression library samples. No effort is made to assure that any specific gene lies within any particular fragment. No mapping of the bacterial DNA in the traditional sense is required. Indeed, the development of a diagnostic procedure according to the present invention theoretically can be carried out with total disregard for the exact chemical composition of the DNA of the infecting bacterial pathogen or of the encoded proteins. Thus, the present invention radically differs from prior art methods by obviating the need to rigorously map the DNA of the infecting bacterial pathogen.

A favored technique for fragmenting the genomic DNA is partial digestion by reaction with a restriction enzyme. The number of fragments is important to the effectiveness of the novel method. That is, a very large number of fragments increases the probability that selectively and discriminatingly responsive protein-producing genes will be effectively isolated on separate fragments.

To understand the degree of fragmentation useful for carrying out the present invention, consider the following hypothetical extremes wherein (i) genomic bacterial DNA is only cut once into two large fragments; and (ii) nearly complete digestion that yields extremely short sequence fragments, e.g., of less than about 21 base pair length. In the first hypothetical, each of the two fragments will contain a vast assortment of genes which are capable of encoding a wide variety of proteins. Consequently, it is very likely that some of the proteins produced by the group of genes in either ultra-large fragment will induce a positive response to almost every animal specimen presented. Thus, extremely incomplete partial digestion probably will not yield fragments containing few enough genes per fragment such that the whole group of proteins obtained therefrom can distinguish between viable or convalescent infection from naive state infection. In the second hypothetical, the number of fragments produced can be so large that time and labor needed to evaluate all the protein groups for immune response activity can be excessive.

The ideal number of fragments and average base pair length of nucleotide sequences per fragment lies within the above hypothetical extremes. It is desirable to cut the DNA so that the average fragment contains at least one protein encoding gene. The optimum fragment number and average base pair length will depend upon the DNA of the infecting bacterial pathogen, and other factors such as the number of proteins of the infecting bacterial pathogen likely to be expressed by a single clone. The novel method of this invention is effective over a broad range of fragment number and average base pair length around the optima. Hence, it is not critical to obtain the precise optimum fragmentation. In view of the present disclosure, one of ordinary skill in the art should be able to select an effective degree of DNA fragmentation without undue experimentation.

One parameter that affects the fragmentation is the frequency of occurrence of the restriction enzyme recognition sequence in the DNA of the infecting bacterial pathogen of interest. Extent of digestion is another parameter that can be used to control fragmentation. The farther that digestion is permitted to proceed toward completion, the shorter and more numerous will be the fragments produced. To determine the conditions that produce near-optimum fragmentation for a particular restriction enzyme selected for a given bacterial pathogen, a series of test digestions can be run. Choosing the range of conditions to run for test digestions can involve some trial and error. However, one of ordinary skill in the art should be able to find test digestion conditions without excessive difficulty. A typical starting point for choosing test digestion conditions is to use one twentieth of the total units of restriction enzyme necessary to completely cleave all recognition sites in a preselected amount of target DNA and varying the duration of the test digestions from one to fifteen minutes. As used herein, the term "unit of restriction enzyme" means the amount of a particular enzyme necessary to completely cleave all recognition sites in 1 μg of target DNA in 1 hour at a selected temperature. The fragmentation resulting from each test digestion can be evaluated by well known electrophoresis techniques. That is, a sample of digestion product is fractionated by electrophoresis through a gel which is stained and examined. A broad spectrum of bands indicates division of the source DNA into an acceptable number of fragments. Based upon the results of the test digestions, digestion conditions can be chosen to provide the preferred large number of fragments.

An expression library should be developed from the effectively large number of fragments of source DNA. A typical method for this involves transfecting the fragments into a host bacteria and growing up the colonies of mutant host. DNA fragments can be transfected into the host using any of the known methods, such as by absorption of the DNA complexed with liposomes of cationic amphiphiles mixed with suitable phospholipids. Particular preference is given to the technique of incorporating the DNA fragments into cosmids and packaging the cosmid constructs into bacteriophage vectors such as viral heads. Numerous cosmids and vector entities are commercially available for these purposes and the selection of a suitable construct/vector system should be well within the ability of one of ordinary skill in this art.

The host bacteria should be different from the infecting bacterial pathogen to avoid introducing cross reactivity. The species of host is not particularly critical. *E. coli* is preferred primarily due to its prevalence in the field of biotechnology. The transfected host can be cultured to clone the proteinaceous products of the cosmid constructs. This will provide effective amounts for subsequent screening steps and to establish a cell line as a continuing source of those protein groups later identified as selectively and discriminatingly responsive.

The present invention chiefly involves screening the protein groups generated by the samples of the expression library. As mentioned, the purpose of screening is to determine reactivity of each sample to antibody-bearing specimens from animals with viable, convalescent and naive state bacterial infections. The animal specimens can be taken from any antibody-bearing tissue, however, it is desirable to obtain specimens non-invasively to minimize risk of harm and discomfort to the patient, and to provide rapid and low cost analyses. Thus diagnostic procedures developed according to the present method preferably employ non-invasively obtained specimens such as peripheral blood and saliva cells. Serum sampling is more preferred.

Reactivity of the expression library samples is tested by any of the recognized immune response assay protocols mentioned above. Because the novel development method fundamentally generates a large number, usually greater than a thousand, of expression library samples, a correspondingly large volume of known infected state samples should be available for the screening process. Especially for the first level of screening to identify the positively responsive protein groups, a very large amount of known viable infection serum can be consumed. Conveniently, such a large known-infected, uniform serum supply can be obtained by hyperimmunization techniques using laboratory animals. For example, lab animals can be iteratively injected directly with the infecting bacterial pathogen under investigation. An immune response to the pathogen is permitted to develop within the lab animal for a period of time between injections which develops a hyperimmune antibody concentration in the animal's serum. The animal used for hyperimmunization is not critical and need not be a primate. However, the animal should be large enough to yield a sufficient quantity of hyperimmune serum that will permit carrying out all of the expected reactivity screening tests. Rabbits are ideal for this purpose. The hyperimmune animal can be sampled prior to initially administering the pathogen and periodically to assure proper antibody development.

When a sufficiently high antibody concentration is developed, serum from the animal can be harvested, normally by exsanguination. Aliquots of the hyperimmune serum are preferably used for a preliminary screening of the expression library samples. When a host bacteria is employed to obtain expression library samples, it is recommended to pre-adsorb the animal specimen with the host bacteria. This step binds antibodies in the specimen to host antigens and thereby eliminates production of electrophoresis bands that would result from reaction to host antigen. The pre-adsorbed hyperimmune animal serum is incubated with the protein group produced by each of the library samples. The product then is examined for evidence of binding of the infecting bacterial pathogen antigen proteins with antibodies. Preferably, the incubation products are separated by migration through electrophoresis gels and reactive bands noted by visual inspection. A band can appear for each protein present in the expression library sample group. Because more than one protein can be present in each group, multiple bands may appear for any single incubation product. Existence of at least one band indicates a positive response.

The hyperimmune animal preliminary screening serves to quickly separate the potentially positively responsive protein groups from non-responsive samples. Such preliminary screening can reduce the number of samples that should be analyzed with actual patient serum by a factor of about ten and commensurately reduces the amount of patient serum required. However, the hyperimmune preliminary screenings should not be substituted for expression library sample screening against specimens from the patient animal for which a particular diagnostic method is being developed.

The potentially positively responsive protein groups of the narrowed population identified by preliminary hyperimmune screening should be screened again but with actual patient animal specimens from a patient known to have viable infection. All of the potentially positively responsive expression library samples can be screened at once or a more manageable subset of them can be screened at first. The object is to identify a reasonably sized set of positively responsive protein groups such that the likelihood of ultimately finding among them selectively and discriminatingly responsive groups is good. More of the potentially positively responsive samples can be screened later if selectively and discriminatingly responsive groups are not found among the first subset. If a hyperimmune animal test is used to choose the potentially positively responsive expression library samples, it is often beneficial to retest the reactivity of the chosen expression library samples with hyperimmune specimens alongside the actual infected specimens. This can validate the existence of a positively selective responses. Each band that appears in a blot from an electrophoresis gel indicates positive antigen-antibody interaction.

Protein groups which evoke a response to the specimen from the patient animal with known viable infection of the infecting bacterial pathogen are thus identified as being positively responsive. The expression library samples from which these protein groups were obtained are appropriately noted. Additional protein group samples are harvested from the positively responsive expression library samples. These protein groups are tested for response with first control specimens from patient animals known to be naive with respect to the infecting bacterial pathogen. Those protein groups which do not indicate a response to the first control specimens are identified as selectively responsive. For example, when an electrophoresis gel blot band that had appeared when tested for reaction to the known viable infection specimen does not appear in response to incubation with a naive, first control specimen, the corresponding protein in the group is deemed to not indicate a response. If at least one protein in a positively responsive group does not indicate a response to the first control specimen, that group becomes identified as selectively responsive. Note is made of the expression library samples from which the selectively responsive protein groups were obtained.

The selectively responsive group of expression library samples can be culled further in another level of screening. Fresh protein groups from the selectively responsive library samples are tested for reaction to second control specimens from patient animals known to be convalescent with respect to the infecting bacterial pathogen. Such protein groups that do not indicate a response to the second control specimens are identified as discriminatingly responsive. That is, these proteins demonstrated the ability to respond to viable infection but neither to naive state nor to convalescent infection. A determination that a selectively responsive group is not responsive to the second control is made for example, when the same electrophoresis gel blot band that had appeared when tested for reaction to the known viable infection specimen and did not appear in response to incubation with a naive, first control specimen also does not appear in response to incubation with the second control. If at least one protein in a selectively responsive group does not indicate a response to the second control specimen, that group is identified as discriminatingly responsive and note is made of the expression library samples from which the discriminatingly responsive protein groups were obtained.

Each of the selectively responsive protein groups and discriminatingly responsive protein groups can be used independently to diagnose a particular condition of a suspected patient. That is, by contacting a specimen from a patient of unknown infection condition with a selectively responsive protein group, the failure to develop an immune response can tell the diagnostician whether the patient is naive with respect to the infecting pathogen. However, the development of an immune response by this test does not reveal whether the patient is viable or convalescent. Although selectively responsive protein groups are identified by their positive response to viable infection, it is possible that a selectively responsive protein will also respond to a convalescent state of infection. Similarly, a discriminatingly responsive protein group does not produce an immune response to both convalescent and naive states of infection. This is because discriminatingly responsive proteins do not respond to first and second control specimens. Consequently, an unknown patient testing positive by a discriminatingly responsive protein can be diagnosed with viable infection. However, a negative result from a discriminatingly responsive protein test cannot tell whether the unknown has no infection or a convalescent infection. Hence it is seen that to fully characterize a patient, two diagnostic procedures should be used together in circumstances either when an unknown patient tests positive by a selectively responsive protein test or tests negative by a discriminatingly responsive protein test. In the two diagnostic procedures, one should employ a discriminatingly responsive protein group and the other a selectively responsive protein group that is not also discriminatingly responsive.

This invention is now illustrated by examples of certain representative embodiments thereof, wherein all parts, proportions and percentages are by weight unless otherwise indicated. All units of weight and measure not originally obtained in SI units have been converted to SI units. Solutions referred to herein are described in Table I.

EXAMPLE 1

A composition useful for diagnosing Hp infection in humans was produced according to the following procedures. During the performance of these procedures intermediate products were stored at 4° C., unless otherwise indicated, as necessary until materials or prerequisite procedures had been appropriately prepared or completed. Some of these refrigerated storage steps are not stated in the description of the example.

TABLE I

| | Buffer B 10X | CIAP Buffer 10X | Buffer D 10X | Buffer E 10X | 10X (T4 DNA Ligase Buffer) | LB** Broth | SM Buffer | Sample Buffer |
|---|---|---|---|---|---|---|---|---|
| Tris-HCl | 60 mM | 0.5 M | 60 mM | 60 mM | 300 mM | 50 ml of 1 M | | 50 mM |
| pH of Tris-HCl | 7.5 | 9.0 | 7.9 | 7.5 | 7.8 | — | 7.5 | 8.4 |
| NaCl | 500 mM | — | 1.5 M | 1.0 M | — | 10 g | 5.8 g | — |
| $MgCl_2$, mM | 60 | 10 | 60 | 60 | 100 | — | — | — |
| DTT$^{(1)}$, mM | 10 | — | 10 | 10 | 100 | — | — | 100 |
| $ZnCl_2$, mM | — | 1 | — | — | — | — | — | — |
| Spermidine, mM | — | 10 | — | — | — | — | — | — |
| Tryptone, g | — | — | — | — | — | 10 | — | — |
| Yeast extract, g | — | — | — | — | — | 5 | — | — |
| $MgSO_4 \cdot 7\ H_2O$ | — | — | — | — | — | — | 2.0 g | — |
| 2% (w/v) Gelatin | — | — | — | — | — | — | 5 ml | — |
| Deionized $H_2O$ | — | — | — | — | — | — | *** | — |
| ATP$^{(2)}$, mM | — | — | — | — | 10 | — | — | — |
| Glycerol, wt % | — | — | — | — | — | — | — | 10 |
| SDS$^{(3)}$, wt % | — | — | — | — | — | — | — | 2 |
| Bromphenol Blue, wt % | — | — | — | — | — | — | — | 0.1 |

$^{(1)}$Dithiothrietol
$^{(2)}$Adenosine 5'-triphosphate
$^{(3)}$Sodium dodecylsulfate
**ingredients dissolved in deionized water adjusted to pH 7.0 using 5 N NaOH and brought up to a final volume of 1L.
***amount effective to total 1L.

I Obtaining DNA From *Helicobacter pylori*

(a) Harvest HP DNA

Lyophilized pellets of *Helicobacter pylori* obtained from the American Type Culture Collection accession number 43504 were reconstituted in a sterilized tissue culture flask under carbon dioxide at 37° C. in brucella broth medium containing cyclodextrin. After the biomass became turbid as observed by visual inspection the Hp was plated onto Skirrows medium (Becton Dickinson, Cockeysville, Md.) and grown under $CO_2$ for 10 days. The scrapings from all the plates were placed in a tube and then the Hp was washed five times with 5 mM magnesium chloride in phosphate buffered saline (PBS). Each wash was centrifuged, the medium decanted and the Hp resuspended. After the fifth wash, the Hp was resuspended in 5 mM $MgCl_2$/PBS and stored at −80° C. in preparation for DNA extraction.

The procedure of Sambrook, J., Fritsch, E. F., and Maniatis, T., *Isolation of DNA from Mammalian Cells: Protocol III*, Molecular Cloning, A Laboratory Manual, 2nd, Ed., Cold Spring Harbor Laboratory Press, Vol. 2, pp. 9.22–9.23 (1989) was modified to extract the DNA, as follows. After thawing, 100 μL harvested Hp suspension was mixed with 750 μL lysis solution of 6 M guanidine HCl and 0.1 M sodium acetate at pH 5.5 in sterile, reverse osmosis purified water. The mixture was incubated for 1 hour at room temperature on a platform shaker, then centrifuged in a Beckman Micro 12 centrifuge at a setting of 12.5 for thirty minutes at 4° C.

(b) Extraction Procedure

The supernatant liquid was aspirated to a clean container to which an equal volume of solution of 25 volume parts phenol, 24 volume parts chloroform and 1 volume part isoamyl alcohol (IAA) was added. The combined materials were mixed by vortexing and inverting the container, after which the product was centrifuged and the resulting supernate was pipetted to another clean container. This solvent separation was repeated with a solution of 24 volume parts chloroform and 1 volume part IAA solution and the upper phase centrifuge product was collected.

To precipitate the DNA, 0.1 volume part of 3M sodium acetate and 2.5 volume parts 95% ethyl alcohol were added to the centrifuge supernate in a microcentrifuge tube which was inverted several times to mix the ingredients. The mixture was centrifuged at 4° C. for 30 minutes in the Micro 12 centrifuge at a setting of 12.5 and a white pellet was collected by decanting the supernate. The pellet was washed by addition of 1 ml of 70% ethyl alcohol. The wash was spun for 2 minutes to compact the pellet after which the liquid was decanted and the pellet was freeze dried. The DNA was resuspended in tris-EDTA buffer consisting of 10 mM tris (hydroxymethyl)-aminomethane ("Tris") and 1 mM ethylene diamine tetraacetic acid ("EDTA") to a total volume of 200 μL. The suspended DNA was stored at −20° C. until ready for use.

(c) DNA Quality Check

Purity and concentration of the DNA in the extraction product were confirmed by well known spectrophotometric absorbance methods. The ratio of absorbance at 260 nm wavelength to absorbance at 280 nm wavelength, i.e., ($A_{260}/A_{280}$), of the resuspended DNA was measured to be in the range of about 1.6–2.0.

Partial Digestion of *Helicobacter pylori* DNA

Restriction buffer B of Promega, Madison, Wis., supplied at 10× was diluted to 1× with sterile water. Restriction enzyme Sau3A I from Promega supplied at 10 units/μL was diluted with 1× Promega buffer A to provide 0.667 units per μL. One μL of diluted Sau3A I was added to 13.5 μg harvested Hp DNA in a fresh tube. Promega 10× restriction buffer was added to the tube in amount necessary to yield 1× buffer concentration. The restriction enzyme was permitted to react with the DNA for 10 minutes at 37° C. then the enzyme was inactivated by placing the tube in a 70° C. water bath for 5 min. A 1 μg aliquot of the digestion product was evaluated by electrophoresis using a 0.4% agarose gel. Voltage was adjusted as necessary to obtain good separation of the fragments. Visual observation confirmed that the partial digestion had produced a broad spectrum of DNA fragments. The digested Hp DNA fragments were treated according to the procedure of step I(b) to obtain a 50 μL suspension in tris-EDTA.

The digested Hp DNA was treated with 2.5 units of calf intestinal alkaline phosphatase (CIAP) enzyme per 50 pmols of 5' termini to remove terminal phosphates, as follows: Promega 10× CIAP buffer was diluted to 1× with sterile water. Promega CIAP was diluted with 1× CIAP buffer to 0.125 units/μL concentration. One μL of diluted CIAP was combined with the 50 μL of digested Hp DNA fragments, 10 μL of 10× CIAP buffer and sterile water to total 100 μL. The mixture was incubated at 37° C. for 1 hour. The enzyme was inactivated by addition of 3 μL 0.5 M EDTA and holding the sample at 68° C. for 10 minutes. This product was treated according to the procedure of step I(b) to produce a suspension of the resulting pellet in Tris EDTA to a total volume of 12.5 μL.

III Preparation of Cosmid

SuperCos I cosmid vector from Stratagene, La Jolla, Calif. was linearized by digestion with Xba I restriction enzyme from Promega according to the following procedure. A map of SuperCos I is shown in FIG. 1. A 25 μg portion of SuperCos I supplied at 1 μg/μL concentration was combined with 20 μL of Promega 10× restriction buffer "D", 18.75 μL XbaI corresponding to 225 units of enzyme and sufficient sterile water to make 200 μL total. The mixture was held at 37° C. for 1 hour then inactivated at 65° C. for 15 minutes. A 1 μg aliquot of cosmid digestion product was taken and the remainder was stored at −20° C. The aliquot was subjected to electrophoresis using a 0.8% agarose gel. This test produced a band at 7.6 K base pairs which confirmed that the cosmid had linearized. The linearized vector was treated according to the procedure of step I(b). The pellet of linearized SuperCos I was suspended in tris-EDTA to a total of 24 μL.

The linearized cosmid vector was treated with 2.5 units of CIAP per 50 pmols of 5' termini to remove terminal phosphates. Promega CIAP was diluted with 1× CIAP buffer to 0.5 units/μL concentration. One μL of diluted CIAP was combined with the 24 μL of SuperCos I, 10 μL of 10× CIAP buffer and sterile water to total 100 μL. The mixture was incubated at 37° C. for 1 hour. The reaction was inactivated by addition of 3 μL 0.5 M EDTA and holding the sample at 68° C. for 10 minutes. The product was treated according to the procedure of step I(b) to suspend the resulting pellet in tris-EDTA to a total volume of 24 μL.

The phosphatase-treated cosmid vector was next digested with BamH I enzyme to cleave the linearized vector. The 24 μL of vector in tris-EDTA was combined with 12 μL BamH I supplied by Promega at 10 units per μL concentration; 20 μL of 10× Promega buffer "E"; and 144 μL sterile water. This mixture was incubated for 1 hour at 37° C. Without inactivation, an aliquot of digestion product was tested by electrophoresis separation on a 0.8% agarose gel. Appropriate bands were observed to indicate that a 6.5 K base pair length sequence had been obtained. The digestion product was immediately frozen for temporary storage. Thereafter it was thawed and treated according to the procedure of step I(b) to yield a suspension in 24 μL of tris-EDTA.

IV Ligating DNA Fragments and Vector

In a fresh tube were combined 5 μL of partially digested Hp DNA fragments product of step II; 2 μL linearized SuperCos I suspension product of step III; 2 μL Promega 10× T4 DNA Ligase Buffer; 2 μL of 10 mM ATP from Sigma, St. Louis, Mo.; and 9 μL sterile water. The composition was mixed gently by inverting the tube. A 1 μL aliquot was withdrawn and refrigerated for use as a control sample.

Promega 10× T4 DNA Ligase Buffer was diluted with sterile water to 1× concentration. The 1× T4 ligase buffer was used to dilute T4 DNA ligase enzyme from 3 units/μL as supplied by Promega to 2 units/μL. One μL of the dilute T4 DNA ligase was added to the remaining 19 μL of Hp DNA fragment composition. The composition was then mixed by inverting the tube and allowed to react overnight at 4° C. The reaction produced a multitude of cosmid constructs containing random length Hp DNA fragments.

V Packaging Cosmid Into Bacteriophage

The Hp DNA-bearing cosmid constructs were packaged into bacteriophage heads in accordance with the procedures of the "Gigapak II-XL" kit of Stratagene. Stratagene's sonic extract was thawed in a bucket of ice. Stratagene's freeze-thaw extract was thawed just enough to begin melting. To the freeze-thaw extract in a centrifuge tube was added 4 μL of the ligation reaction product of step IV. Immediately thereafter, 15 μL of sonic extract was added and the composition was gently stirred by pipette so as not to introduce air bubbles into the liquid. The composition was permitted to stand at room temperature for 100 minutes. Then 500 μL of autoclaved SM buffer and 20 μL chloroform were added. The resulting composition was gently mixed by inverting the tube. Thereafter the tube was centrifuged for 2 minutes at about 7,000×g and the supernate was transferred to a fresh tube. The packaged cosmid constructs in the expression library prepared from the 10 minute partial digestion ("Lib-10") were refrigerated while being stored for subsequent use.

VI Generating Additional Digestion Products

Steps II through V were repeated two additional times in substantially the same manner as described using Hp DNA prepared according to step I, except that partial digestion of Step II was carried out for 1 minute and 5 minutes to obtain expression libraries Lib-10 and Lib-5, respectively.

VII Providing Host Organism

Shavings of frozen XL1-blue MR strain of *Escherichia coli* (*E. coli*) from Stratagene were streaked onto a plate of LB agar medium. After incubation at 37° C. overnight, an isolated colony was transferred into a tube of 1 0 ml LB broth. The *E. coli* was shaker-incubated at 37° C. overnight. To the culture was added 4.5 ml of glycerol media solution consisting of 5 ml sterile glycerol and 5 ml LB broth. After gentle mixing with mild shaking, the culture was subdivided into multiple tubes and stored at −80° C. until needed.

Shavings from one of the frozen glycerol stock cultures were streaked onto a fresh plate of LB agar medium. The plates were incubated at 37° C. overnight. An isolated colony was transferred into a culture tube to which 50 ml of medium was added. This medium consisted of LB broth plus 10 mM magnesium sulfate and 2% maltose. The culture tube was incubated in a shaker incubator at 37° C. After 6 hours, a 1 ml aliquot was tested for spectrophotometric absorbance at 600 nm wavelength. An absorbance between 0.8 and 1.0 was measured which indicated that incubation had been sufficiently completed. The culture was poured into a 50 ml centrifuge tube and spun at 500×g for 10 minutes at 4° C. The pellet was resuspended in 25 ml of sterile 10 mM magnesium sulfate solution and then refrigerated while stored.

VII Cloning Host Organism With Cosmid Construct

The suspended *E. coli* product of Step V was diluted with sufficient additional magnesium sulfate to produce a spectrophotometric absorbance of 0.5 at 600 nm wavelength. Aliquots of samples from Lib-1, Lib-5 and Lib-10 were each diluted 1:10 and 1:50 with SM buffer.

Three 25 μL samples of the diluted *E. coli* were transfected with 25 μL Lib-1, and the 1:10 and 1:50 Lib-1 dilutions, respectively. The combined samples were preliminarily incubated at room temperature for 30 minutes then 200 μL of LB broth was added to each. The samples were then incubated further for one hour at 37° C. The transfection products each were centrifuged at about 7000×g then resuspended to 50 μL in fresh LB broth. Each sample was streaked in duplicate on separate plates of LB agar medium that additionally contained 50 μg/ml ampicillin. The six plates were incubated overnight at 37° C. then stored at 4° C. This procedure for transfecting E. coli with Lib-1 was repeated to generate six additional refrigerated plates. The whole cultures developed on the total of twelve plates were transferred into a single 15 ml tube ("T-1") by scraping and flushing with drops of LB broth. Glycerol with 50 μg/ml ampicillin was added to the tube to a concentration of 18 vol. %. This transfection procedure was repeated with a single mixture of 150 μL of the remaining Lib-1 and 150 μL diluted E. coli to produce another 15 ml tube of transfected host in 18 vol. % glycerol. Aliquots of the product were placed in multiple 1.5 ml tubes which were frozen at −80° C. ("T-2").

In the same manner as just described, 25 μL diluted E. coli was transfected with 25 μL portions of Lib-5 and the Lib-5/SM buffer solutions to yield a single tube ("T-3") of transfected product stabilized with 18 vol. % glycerol. Similarly, 150 μL of Lib-5 and diluted E. coli were mixed and incubated to produce tubes of transfected host ("T-4").

A fifth sample of transfected host was generated from the Lib-10 product as follows. Three 25 μL samples of diluted E. coli were transfected with 25 μL Lib-10 and the 1:10 and 1:50 Lib-10/SM buffer solutions, respectively. The procedure used for transfecting with Lib-1 and Lib-5 was repeated except that the transfected host colonies were individually picked off the plates rather than transferred by scraping. One hundred microliters of undiluted Lib-10 was transfected into a like amount of E. coli. The products of all of the Lib-10 transfections were combined into a single tube ("T-5") stabilized with ampicillin and glycerol to 18% volume and frozen.

VIII Culturing Host Organism to Produce Proteins (a) First Colony Population

LB broth titers were prepared with samples of T-1 through T-5 incubated at 37° C. overnight to determine the concentration of colony forming units ("CFUs") present in each. This protocol generated 36 plates. Based on the CFU titer information, transfected host stocks T-2, T4 and T-5 were diluted serially to provide 12 samples of different stock-concentration combinations projected to yield about $5 \times 10^4$ CFUs per culture plate. The 12 stock-concentration combinations were plated in duplicate onto LB agar medium with ampicillin and grown at 37° C. overnight. From among the total of 60 CFU titer plates and stock-concentration combination plates about half yielded a total of 1,234 colonies which were selected for further use. These were individually picked with sterile sticks and inoculated into wells of 96-well microtiter plates. Each well was pre-loaded with 200 μL LB broth containing 50 μg/ml ampicillin. The microtiter plates were incubated at 37° C. overnight. Thereafter glycerol was added to each well to a concentration of 18 vol. % and the microtiter plates were stored at −80° C.

Each plate was placed on a pan of dry ice to cause the cultures to thaw only partially. Samples from each well were taken by individually stabbing with a wooden stick and were inoculated into sterile 15 ml conical tubes containing 5 ml of LB broth and 50 μg/ml ampicillin. The cultures were grown overnight in a shaker incubator at 37° C. Some of the grown cultures were harvested directly for protein according to step IX, below. Most cultures were heat treated before harvesting to kill the E. coli primarily for safety purposes by placing the conical tubes in a 56° C. water bath for 2 hours.

Each sample was centrifuged to collect the cells in a pellet. Supernatant culture medium was aspirated into a vacuum trap containing bleach. The pellet was suspended in 1 ml of sterile PBS by machine vortexing. The sample was transferred into a tube, centrifuged, aspirated and resuspended repeatedly for a total of three such washes. After the third wash, the pellet was resuspended in 500 μL PBS and stored at −80° C.

(b) Second Colony Population: An additional 287 transfected E. coli colonies chosen from the 60 CFU titer plates and stock-concentration combination plates were picked with a wooden stick for inoculation into a culture tube of 5 ml of LB broth and 50 μg/ml ampicillin. The colonies were incubated stationary at 37° C. for two days at which time a 1 ml aliquot was placed in a 1.5 ml tube. Glycerol to 18 vol. % was added and the aliquots were stored at −80° C. Each approximately 4 ml residual colony sample was further incubated at 37° C. for another night. The sample was centrifuged and washed in sterile PBS as in step VIII (A.) to yield a frozen 500 μL suspension.

IX Harvesting Protein

From the total of 1,521 cultured E. coli colonies of steps VIII (a) and (b), 741 from Lib-1, 508 from Lib-5 and 218 from Lib-10 were harvested for proteins as follows. Frozen samples were thawed to room temperature. Each sample was subjected to two 10 second blasts at a sonication setting of 4.0 using a model W185 Sonifier Cell Disrupter (Heat Systems-Ultrasonics, Inc., Farmingdale, N.Y.) equipped with a microtip. The sonicated sample was held on ice or in a refrigerator until assayed for protein content.

Protein assays were determined with a protein microassay procedure (Bio-Rad, Richmond, Calif.) according to the manufacturers instructions. A series of known bovine gamma globulin protein concentration standards were prepared, incubated for 30 minutes and analyzed at 595 nm wavelength to obtain a standard correlation of concentration with instrument reading. Approximately 5 μL of sonicated product was combined with 795 μL sterile water and 200 μL Bio-Rad dye reagent concentrate and mixed by vortexing. This mixture was analyzed and the sonicated product portion was diluted as necessary to produce a reading on the instrument scale. A raw protein analysis was obtained by reference to the standard correlation and was then corrected for any dilution. After protein assay, harvested E. coli protein samples were stored at −20° C. for further processing.

X Screening Harvested Proteins (a) Producing Hyperimmune Rabbit Serum

Hp (ATCC accession No. 43504) grown in Skirrows medium and stored in 5 mM $MgCl_2$PBS as described in step I (a) was killed by exposure to 56° C. for 2 hours before freezing. The dead Hp was sonicated on ice in the Sonifier Cell Disrupter at a setting of 4 using ten blasts of 30 seconds duration each. The resulting product was maintained on ice. Protein content of this product was determined by Bio-Rad protein assay to be 21.2 mg/ml.

Blood samples were taken from two male New Zealand White rabbits for later confirmation of initial non-infection by Hp. The rabbits were then injected in each of 5 subcutaneous locations with 0.2 ml of a 1 mg/ml concentration suspension of Hp product diluted 50/50 (vol/vol) with Incomplete Freund's Adjuvant (Sigma). This injection protocol was repeated on the 18th, 29th, 64th and 96th days after initial injections. On the 18th day 1 ml blood samples were taken from each rabbit, allowed to clot, centrifuged for 5 minutes at 15,000×g and the serum frozen at −80° C. for future testing.

On the 76th day 1 ml blood samples were taken from the rabbits, clotted and centrifuged as before. These blood samples were tested by Western Blot for development of immunity, as follows:

(1) Additional frozen Hp (ATCC accession no. 43504) from Step X(a) was sonicated and assayed for protein content, as above. A 1.488 mg aliquot of Hp protein was diluted to 50 vol. % in Sample Buffer to yield a total volume of 0.372 ml which was then heated to 100° C. for 4 minutes. Proteins were separated using 120 mm×250 mm×2 mm sheets of 11% polyacrylamide electrophoresis gel. The recipe per 100 ml gel consisted of 36.64 ml BioRad 30% Acrylamide/Bis 37.5:1, 20.0 ml 1.88 M Tris-HCl (pH 8.8), 512 μL of 20% SDS in deionized water, 42.24 ml deionized water, 56 μL Tetramethyl ethylenediamine ("TEMED"), and 560 μL 10% ammonium persulfate ("APS") in deionized water. Protein separation was carried out in an LKB Multiphore-II electrophoresis unit (Pharmacia Biotech, Piscataway, N.J.) operated at 525 V for 3 hours. Separated proteins were transferred to nitrocellulose membranes (Schleicher & Schuell, Keene, N.H.) using a semi-dry Nova blot transfer system (Pharmacia Biotech) in the LKB Multiphore-II unit with 200 mA per gel applied for 1 hour. Blotted membranes were blocked with 0.5% bovine serum albumin in PBS overnight, air dried at room temperature and cut to strips.

(2) The rabbit sera samples were diluted to 1:1000 in PBS with 1% nonfat dry milk and incubated on the test strips for 1 hour at room temperature. The test strips were washed three times with PBS then incubated with a 1:1000 dilution of biotinylated goat anti-rabbit IgG (Kirkegaard & Perry Labs, Gaithersburg, Md.) for 1 hour at room temperature. The strips were again washed three times with PBS and then incubated with a 1:1000 dilution of peroxidase conjugated streptavidin (Kirkegaard & Perry Labs) for 1 hour at room temperature. After three additional washes in PBS the strips were incubated for 15 minutes at room temperature in the presence of 7.8 mM 4-chloro-1-naphthol diluted to 50 vol. % with a solution of 1 volume part 30% aqueous hydrogen peroxide per 1500 volume parts Citrate Phosphate Buffer pH 4.0 (0.2 M $Na_2HPO_4$ and 0.1 M citric acid). Color developed in bands at various locations on the strips confirming that the rabbits had produced antibodies specific to Hp.

On the 105th day after initial injections, the rabbits were sacrificed and exsanguinated. Yield from the rabbits was 150 ml and 90 ml. The blood was clotted and centrifuged at 800×g for 10 minutes. The supernatant serum was frozen and stored at −80° C. prior to use for screening the protein expression libraries.

(b) Screening Protein Libraries With Hyperimmune Rabbit Serum

A Western Blot for each sample of the groups of harvested proteins from expression libraries Lib-1, Lib-5 and Lib-10 prepared in step IX was run to detect immune responses to the hyperimmune rabbit serum. These Western Blots used a "mini-gel" procedure substantially the same as that of step X (a) except as follows: The smaller Mini-gel 11% polyacrylamide sheets from Hoeffer, Piscataway, N.J. were used. Each expression library sample was diluted to 50% with Sample Buffer and heated to 100° C. for 4 minutes, as above. Normally 10 per gel of 20 μL of these expression library samples were loaded into the Mini-gel wells and electrophoresed at 20 mA per gel for 1 hour in a Hoeffer electrophoresis chamber using electrode buffer of 0.192 M glycine, 0.025 M Tris and 0.1% SDS. The separated proteins of the expression library samples were transferred to nitrocellulose as above except that the LKB Multiphore-II unit was run at 50 mA per gel for 1 hour. Blotted membranes were blocked with 0.5% bovine serum albumin in PBS overnight, air dried at room temperature and retained in whole sheet form.

The hyperimmunized rabbit serum was pre-adsorbed to prevent false responses to cross reactive antibodies to the *E. coli*. Serum samples were diluted 1:50 with a solution of 50 vol. % *E. coli* product of step VII and 50 vol. % PBS. They were incubated overnight at 5° C. then centrifuged in the Micro 12 centrifuge for 5 minutes. The supernatant fluid was brought to working dilution of 1:1000 in PBS with 1% nonfat dry milk. The nitrocellulose sheets with expression library sample proteins were reacted with the pre-adsorbed rabbit serum as described in (a)(2), above.

(c) Results of Rabbit Serum Screening

Of the 1,467 harvested expression library samples of step IX, 346 produced positive Western Blot responses to the hyperimmune rabbit serum. From the positively responding sample set, 59 expression library samples were selected for determination of sensitivity to human sera. Selection was based primarily on the strength of the response, i.e., generally, samples which generated the most intense Western Blot bands were selected. As an additional control procedure 4 expression library samples that had not responded to hyperimmune rabbit serum were also chosen for human sera testing. All of the selected samples coincidentally came from the first colony population of step VIII (a).

XI Determining Positively Responsive Proteins (a) Producing Western Blot Strips

For each of the 63 selected expression library samples, cultures were grown to a sufficient size to produce multiple Western Blot strips according to the following procedure. The appropriate 96-well microtiter plate of step VIII (a) was thawed partially on dry ice and samples were taken by individually stabbing the selected well with a wooden tool. The samples were inoculated into sterile 15 ml conical tubes containing 5 ml of LB broth and 50 μg/ml ampicillin. The cultures were grown overnight in a shaker incubator at 37° C. then heat treated before harvesting to kill the *E. coli* by placing the conical tubes in a 56° C. water bath for 2 hours.

Each sample was centrifuged to collect the cells in a pellet. Supernatant culture medium was aspirated into a vacuum trap containing bleach. The pellet was suspended in 1 ml of sterile PBS by machine vortexing. The sample was transferred into a tube, centrifuged, aspirated and resuspended repeatedly for a total of three such washes. After the third wash, the pellet was resuspended in 5 ml PBS and stored at −80° C.

Frozen samples were thawed to room temperature. Each sample was subjected to two 10 second blasts at a sonication setting of 4.0 using a model W185 Sonifier Cell Disrupter (Heat Systems-Ultrasonics, Inc., Farmingdale, N.Y.) equipped with a microtip. The sonicated sample was held on ice or in a refrigerator until assayed for protein content. After protein assay, as in step IX, harvested *E. coli* protein samples were stored at −20° C. for further processing. Each selected expression library sample was diluted to 50% with Sample Buffer and heated to 100° C. for 4 minutes. The sample was placed in the well of a trough-format, 11% polyacrylamide "Mini-gel" sheet. The sheet was electrophoresed at 20 mA per gel for 1 hour in a Hoeffer electrophoresis chamber using electrode buffer of 0.192 M glycine, 0.025 M Tris and 0.1% SDS as in step X (b). The separated proteins were transferred to nitrocellulose as in step X(b) with the LKB Multiphore-II unit run at 50 mA per gel for 1 hour. Blolted membranes were blocked with 0.5% bovine serum albumin in PBS overnight, and air dried at room temperature. Lastly, the nitrocellulose sheets were cut to multiple identical strips.

(b) Viably Infected Human Serum A1

Peripheral blood samples were drawn from a human patient (patient "A1") who was known to have a viable infection of Hp. Human Serum A1 was clotted and centrifuged at 800×g for 10 minutes. The supernatant serum was frozen and stored at −80° C. temporarily.

The active status of Hp infection of patient A1 was verified by several independent diagnostic methods. The patient was clinically examined by a gastroenterologist. The examination included endoscopy and biopsy. The biopsy indicated positive for gastritis and for organisms. CLO testing also was positive. Additionally, a Western Blot test for sensitivity to whole Hp antigen was conducted on the Human Serum A1 as follows. Nitrocellulose membranes were prepared using Hp as in step X(a)(1). Western Blots were run on these membranes using serum from patient A1 as in Step X (a)(2) except that the serum samples were diluted 1:100 and the nitrocellulose was incubated in one case with biotinylated anti-human IgG, and in the other, with biotinylated anti-human IgA antibodies. Both Western Blots developed color which was consistent with diagnosis of the patient's active Hp infection status.

(c) Western Blotting Human Serum A1

The Human Serum A1 was pre-adsorbed by dilution 1:50 with a solution of 50 vol. % E. coli product of step VII. and 50 vol. % PBS. It was incubated overnight at 5° C. then centrifuged in the Micro 12 centrifuge for 5 minutes. The supernatant fluid was brought to working dilution of 1:100 in PBS with 1% nonfat dry milk.

This diluted Human Serum A1 was incubated on strips prepared from each of the 63 expression library samples for 1 hour at room temperature. The test strips were washed three times with PBS then incubated with a 1:1000 dilution of biotinylated anti-human IgG (Kirkegaard & Perry Labs, Gaithersburg, Md.) for 1 hour at room temperature. The strips were again washed three times with PBS and then incubated with a 1:1000 dilution of peroxidase conjugated streptavidin (Kirkegaard & Perry Labs) for 1 hour at room temperature. After three additional washes in PBS the strips were incubated for 15 minutes at room temperature in the presence of 7.8 mM 4-chloro-1-naphthol diluted to 50 vol. % with a solution of I volume part 30% aqueous hydrogen peroxide per 1500 volume parts Citrate Phosphate Buffer pH 4.0 (0.2 M $Na_2HPO_4$ and 0.1 M citric acid).

(d) Results of Human Serum A1 Western Blots

For control purposes, a Western Blot was carried out on duplicates of each of the 63 sample strips using hyperimmune rabbit serum as described in step X(b). Strips tested with Human Serum A1 were placed alongside corresponding rabbit serum strips for comparison. All of the four expression library samples which had earlier failed to respond to hyperimmune rabbit serum again did not respond. Furthermore, these same samples did not respond to Human Serum A1. Bands developed on each of the 59 previously positive rabbit serum controls and some Human Serum A1 Western Blot strips. Comparison of the Human Serum A1 strip and corresponding rabbit serum strips revealed that 17 Human Serum A1 strips contained at least one matching band associated with a positively responsive protein.

XII Determining Selectively Responsive Proteins

Identify a human patient (patient "N1") who is naive to H. pylori infection. Determine naive status by examining the patient endoscopically and by obtaining a biopsy sample. Test the biopsy sample for gastritis and organisms by methods described in step XI. Verify that gastritis and organism assay results are negative. Draw peripheral blood samples from patient N1, and clot, centrifuge and freeze Human Serum N1 until ready for use.

Pre-adsorb the Human Serum N1 with E. coli product of step VII then incubate, centrifuge and dilute the pre-adsorbed Human Serum N1 as in step XI (c). Prepare Western Blot strips from each of the 17 expression library samples which produced a positive response to Human Serum A1. Incubate and treat the diluted Human Serum N1 on the 17 strips according to the protocol of step XI (c). Observe that strips from three expression library samples, namely, 1D153, 1C50 and 1D80 do not produce an immunization response. Identify the expression library samples corresponding to these three strips as selectively responsive protein group containing samples.

XII Determining Discriminatingly Responsive Proteins

Identify a human patient (patient "C1") who was previously diagnosed as having viable H. pylori infection, was successfully treated and does not presently exhibit symptoms of gastritis or H. pylori infection. Verify infection status by examining the patient endoscopically and by ELISA and CLO test. Results of endoscopy reveal that viable H. pylori organisms are not present. Further, CLO assay is negative. ELISA results are positive confirming patient's prior infection. Draw peripheral blood samples from patient C1, and clot, centrifuge and freeze Human Serum C1 until ready for use.

Pre-adsorb the Human Serum C1 with E. coli product of step VII then incubate, centrifuge and dilute the pre-adsorbed Human Serum C1 as in step XI (c). Prepare Western Blot strips from each of the 17 expression library samples which produced a positive response to Human Serum A1. Incubate and treat the diluted Human Serum C1 on the 17 strips according to the protocol of step XI (c). Observe that strips from three expression library samples, namely, 1D153, 1C50 and 1D80 do not produce an immunization response. Identify the expression library samples corresponding to these three strips as discriminatingly responsive protein group containing samples.

EXAMPLES 2–15

Fourteen human patients with either naive (Exs. 2–5), viable (Exs. 6–10) state infection, or successfully treated prior H. pylori infection (Exs. 11–15) were identified. Diagnoses of these patients' conditions were made by clinical studies including visual examination via endoscopy, and CLO and culture tests of samples sectioned from the patient during endoscopic examination. Peripheral blood samples drawn from these patients were subjected to an FDA-approved, commercial in vitro ELISA assay and a customized Western Blot analysis based on whole H. pylori bacteria, as described in step XI(b) of Example 1. No endoscopy, CLO and culture assays were performed on the naive state patients. No Western Blot or culture test was performed on samples from Ex. 11–15 patients. The results shown in Table II confirm the state of each patient's infection status.

Samples 1D153, 1D80 and 1C50 from expression library Lib-1 were chosen as representative discriminatingly responsive protein containing groups. Clones of these samples were used to generate nitrocellulose membranes according to the procedure described in step XI (a)(1) of Example 1. Western Blots using strips cut from the nitrocellulose membrane were run with clones from each of the three expression library samples and the responses evoked are summarized in Table II. From the table it is seen that all naive state controls were non-reactive to the library sample clones. Further, the 1C50 and ID80 library sample clones generated a positive reaction to the blood from all viably infected patients and the 1D153 library sample clone produced a positive response in three of the five known viable infections.

In Exs. 11–15, lingering antibodies from prior infection triggered positive ELISA results although endoscopy and CLO testing showed that no detectable viable organisms were present in these successfully treated patients. Negative results of tests with expression library samples demonstrated that clones 1D153, 1D80 and 1C50 were discriminatingly responsive.

TABLE II

| | | Status Diagnosis Confirmation Method | | | | | Response To This Method | | |
|---|---|---|---|---|---|---|---|---|---|
| | Infection | ELISA | Western Blot | Endo- | | | | | |
| | Status | G/A | G/A | scopy | CLO | Culture | 1D153 | 1C50 | 1D80 |
| Ex. 2 | Naive | −/− | −/− | ND | ND | ND | — | — | — |
| Ex. 3 | Naive | −/− | −/− | ND | ND | ND | — | — | — |
| Ex. 4 | Naive | −/− | −/− | ND | ND | ND | — | — | — |
| Ex. 5 | Naive | −/− | −/− | ND | ND | ND | — | — | — |
| Ex. 6 | Active | +/+ | +/+ | + | — | — | + | + | + |
| Ex. 7 | Active | +/− | +/− | + | + | + | + | + | + |
| Ex. 8 | Active | +/+ | +/− | + | + | + | — | + | + |
| Ex. 9 | Active | +/+ | +/− | + | + | + | + | + | + |
| Ex. 10 | Active | +/+ | +/− | — | + | + | — | + | + |
| Ex. 11 | Inactive[1] | +/− | ND | — | — | ND | — | — | — |
| Ex. 12 | Inactive[1] | +/− | ND | — | — | ND | — | — | — |
| Ex. 13 | Inactive[1] | +/+ | ND | — | — | ND | — | — | — |
| Ex. 14 | Inactive[1] | +/− | ND | — | — | ND | — | — | — |
| Ex. 15 | Inactive[1] | +/− | ND | — | — | ND | — | — | — |

Legend:
+ Positive Reaction
— Negative Reaction
ND No Data
G/A Response to biotinylated anti-human IgG and IgA antibodies, respectively.
[1]Inactive denotes that patient had no detectable viable organisms by endoscopic examination and had negative CLO test result.

Although specific forms of the invention have been selected for examples, and the preceding description is drawn in specific terms for the purpose of describing these forms of the invention, this description is not intended to limit the scope of the invention which is defined in the claims.

What is claimed is:

1. A method for developing a diagnostic procedure for detecting a stage of bacterial infection of an animal by an infecting bacterial pathogen comprising the steps of:

(A) producing an animal population antibody profile specific for said infecting bacterial pathogen from animals having various stages of infection from said infecting bacterial pathogen wherein said profile contains a plurality of types antibody in response to said infecting bacterial pathogen;

(B) hyper-immunizing a lab animal with said infection bacterial pathogen so that said lab animal produces serum that has a lab animal antibody profile that substantially matches said animal population antibody profile;

(C) cloning bacteria using fragments of nucleic acid from said infecting bacterial pathogen to produce a plurality of cloned bacteria groups, each cloned bacterial group having been produced using a different fragment of nucleic acid;

(D) culturing each cloned bacteria group separately;

(E) denaturing and separating proteins from each cloned bacteria group;

(F) contacting said denatured proteins from each cloned bacteria group with serum from said lab animals;

(G) selecting said cloned bacteria groups that produce proteins that give a positive immune response to the serum; and (H) using said proteins that give a positive immune response to said serum to diagnose a stage of infection from said infecting bacterial pathogen in an animal.

2. The method of claim 1 wherein in step (F), said contacting is performed with active serum, wherein the active serum is from an animal know to have an active infection.

3. The method of claim 2 further comprising the steps of:

(I) denaturing and separating proteins from said cloned bacteria of said group that have a positive immune response;

(J) contacting denatured and separated proteins from the cloned bacteria of the positively responsive group with naïve serum, wherein said naïve serum is from an animal known to be naïve with respect to infection by said infecting bacterial pathogen; and (K) selecting as a selectively responsive group, each of the cloned bacteria that produced proteins that do not generate an immune response to the naïve serum.

4. The method of claim 3 further comprising steps of:

(L) denaturing and separating proteins from said cloned bacteria of said selectively responsive group;

(M) contacting denatured and separated proteins from said cloned bacteria of said selectively responsive group with convalescent sera, wherein said convalescent sera is from an animal known to be convalescent with respect to said infecting bacterial pathogen; and (N) selecting as a discriminatingly responsive group, each of said cloned bacteria that produced proteins that do not generate an immune response.

5. The method of claim 4 further comprising the step of using proteins generated from said discriminatingly responsive group and said selectively responsive group to diagnose various stages of infection from said infecting bacterial pathogen in an animal.

6. The method of claim 1 wherein said serum is selected from the group consisting of blood serum, saliva, whole blood, blood plasma and body secretion containing antibodies.

7. The method of claim 1 wherein said infecting bacterial pathogen is selected from the group consisting of *Helicobacter pylori* and *Borrelia burgodorferi*.

8. The method of claim 1 wherein said nucleic acid is selected from the group consisting of genomic DNA, plasmid DNA, and combination thereof.

9. The method of claim 1 wherein said animal is a human.

10. A method for producing proteins for detecting a stage of a bacterial infection of an animal by an infecting bacterial pathogen comprising the steps of:

(A) hyper-immunizing a lab animal with said infecting bacterial pathogen so that said lab animal produces serum that has a plurality of antibody types that reflect the antibody types produced by animals during various stages of infection by said infecting bacterial pathogen;

(B) cloning bacteria using fragments of nucleic acid from said infecting bacterial pathogen to produce a plurality of cloned bacteria groups, each cloned bacteria group having been produced using a different fragment of nucleic acid;

(C) culturing each cloned bacteria group separately; and (D) contacting proteins from each cloned bacteria group with serum from said lab animal;

(E) selecting said cloned bacteria groups that produce proteins that give a positive immune response to the serum; and (F) using said proteins that give a positive immune response to said serum to diagnose a stage of infection from said infecting bacterial pathogen in an animal.

11. The method of claim 10 wherein in step (D), said contacting is performed with active serum, wherein the active serum is from an animal know to have an active infection.

12. The method of claim 11 further comprising the steps of:

(G) denaturing and separating proteins from said cloned bacteria of said group that gave a positive immune response;

(H) contacting denatured and separated proteins from the cloned bacteria of the positively responsive group with naïve serum, wherein said naïve serum is from an animal known to be naïve with respect to infection by said infecting bacterial pathogen; and (I) selecting as a selectively responsive group, each of the cloned bacteria that product proteins that do not generate an immune response to the naïve serum.

13. The method of claim 12 further comprising the steps of:

(J) denaturing and separating proteins from said cloned bacteria of said selectively responsive group;

(K) contacting denatured and separated proteins from said cloned bacteria of said selectively responsive group with convalescent sera, wherein said convalescent sera is from an animal known to be convalescent with respect to said infecting bacterial pathogen; and (L) selecting as a discriminatingly responsive group, each of said cloned bacteria that produced proteins that do not generate an immune response.

14. The method of claim 13 further comprising the step of using proteins generated from said discriminatingly responsive group and said selectively responsive group to diagnose various stages of infection from said infecting bacterial pathogen in an animal.

15. The method of claim 10 wherein said serum is selected from the group consisting of blood serum, saliva, whole blood, blood plasma and body secretion containing antibodies.

16. The method of claim 10 wherein said infecting bacterial pathogen is selected from the group consisting of *Helicobacter pylori* and *Borrelia burgdorferi*.

17. The method of claim 10 wherein said nucleic acid is selected from the group consisting of genomic DNA, plasmid DNA, and combination thereof.

18. The method of claim 10 wherein said animal is a human.

* * * * *